United States Patent [19]

Williams et al.

[11] Patent Number: 5,554,610
[45] Date of Patent: Sep. 10, 1996

[54] INHALATIONAL TREATMENT OF PULMONARY HYPERTENSION AND RELATED CONDITIONS

[75] Inventors: Andrew J. Williams; Derek R. Buckle, both of Epsom, England

[73] Assignee: Beecham Group p.l.c., Brentford, England

[21] Appl. No.: 295,220

[22] Filed: Aug. 24, 1994

Related U.S. Application Data

[63] Continuation of Ser. No. 54,711, Apr. 28, 1993, abandoned, which is a continuation of Ser. No. 396,547, Aug. 21, 1989, abandoned, which is a division of Ser. No. 214,776, Jul. 5, 1988, Pat. No. 4,891,380.

[30] Foreign Application Priority Data

Jul. 7, 1987 [GB] United Kingdom ............ 8715944
Aug. 6, 1987 [GB] United Kingdom ............ 8718587

[51] Int. Cl.⁶ ............ A61K 31/54; A61K 31/495; A61K 31/505; A61K 31/44
[52] U.S. Cl. ............ 514/223.2; 514/248; 514/256; 514/260; 514/307; 514/315; 514/392; 514/410; 514/634; 514/929; 514/958
[58] Field of Search ............ 514/260, 223.2, 514/256, 248, 307, 315, 392, 410, 634; 516/356, 929, 958, 692

[56] References Cited

U.S. PATENT DOCUMENTS

| | | | |
|---|---|---|---|
| 2,831,027 | 4/1958 | Pfister, III et al. ............ | 546/460 |
| 3,511,836 | 5/1970 | Hess ............ | 544/291 |
| 4,607,041 | 8/1986 | Baxter et al. ............ | 514/318 |
| 4,617,311 | 10/1986 | Ho ............ | 514/353 |
| 4,855,300 | 8/1989 | Nandi et al. ............ | 514/356 |
| 4,857,312 | 8/1989 | Hegasy et al. ............ | 514/356 |
| 4,885,305 | 12/1989 | Kiechel et al. ............ | 514/356 |

OTHER PUBLICATIONS

Compound 6352 on pp. 848–849 is Merck index, 9th edition (1976).

"Drug Evaluations" Prepared by American Medical Association Dept. of Drugs, Division of Drugs and Technology, 6th Edition (pp. 486–487), 1978.

"Merck Index" No. 6441. (pp. 1031–1032) 11th edition, 1991.

*Primary Examiner*—Kevin E. Weddington
*Attorney, Agent, or Firm*—Hopgood, Calimafde, Kalil & Judlowe

[57] ABSTRACT

A method for the treatment and/or prophylaxis of disorders associated with pulmonary hypertension and/or disorders associated with right heart failure, in mammals, such as humans, which method comprises administering to the mammal in need of such treatment and/or prophylaxis an effective and/or prophylactic amount of a vasodilator selected from the group consisting of ganglion blockers, sympathetic nerve blockers, and direct vasodilators; or a pharmaceutically acceptable salt thereof or a pharmaceutically acceptable solvate thereof.

6 Claims, No Drawings

INHALATIONAL TREATMENT OF PULMONARY HYPERTENSION AND RELATED CONDITIONS

This application is a continuation of application Ser. No. 08/054,711, filed Apr. 28, 1993, now abandoned, which is a continuation of application Ser. No. 07/396,547, filed Aug. 21, 1989, now abandoned, which is a divisional of application Ser. No. 07/214,776, filed Jul. 5, 1988, now U.S. Pat. No. 4,891,380.

The present invention relates to a method for the treatment and/or prophylaxis of disorders associated with pulmonary hypertension.

United Kingdom Patent No. 1489879 discloses the compound N"-Cyano- N-4-pyridyl-N'-1,2,2-trimethylpropylguanidine and, in Example 47, a process by which it can be prepared. The compound, which is referred to herein by its common name, pinacidil, is described in the patent as a hypotensive compound. In "Drugs of the Future" Vol. VI(3), 149, 1981, pinacidil is described as a vasodilator.

It has now been discovered that pinacidil is of potential use in the treatment of disorders associated with pulmonary hypertension and/or of disorders associated with right heart failure, particularly when administered by inhalation. It is also believed that the administration by inhalation of any such vasodilator will be of potential use in the treatment of disorders associated with pulmonary hypertension and/or of disorders associated with right heart failure.

Accordingly, the present invention provides a method for the treatment and/or prophylaxis of disorders associated with pulmonary hypertension and/or disorders associated with right heart failure, in mammals, such as humans, which method comprises administering to the mammal in need of such treatment and/or prophylaxis an effective and/or prophylactic amount of pinacidil; or a pharmaceutically acceptable salt thereof or a pharmaceutically acceptable solvate thereof.

Examples of pharmaceutically acceptable salts of pinacidil include acid addition salts, for example the hydrochloride and hydrobromide salts.

A suitable example of a pharmaceutically acceptable solvate of pinacidil is the hydrate.

Preferably, pinacidil is in substantially pure pharmaceutically acceptable form.

Pinacidil may be prepared as described in the aforementioned U.K. Patent, and pharmaceutically acceptable salts may be prepared conventionally. Hereinafter pinacidil will be referred to as "the Compound".

In an alternative aspect the present invention provides the use of the Compound or a pharmaceutically acceptable salt thereof, or a pharmaceutically acceptable solvate thereof, for the manufacture of a medicament for the treatment and/or prophylaxis of disorders associated with pulmonary hypertension and/or disorders associated with right heart failure.

In particular the present invention provides the use of the Compound or a pharmaceutically acceptable salt thereof, or a pharmaceutically acceptable solvate thereof for the manufacture of a medicament for the treatment and/or prophylaxis of disorders associated with pulmonary hypertension and/or disorders associated with right heart failure.

When used herein the term "pulmonary hypertension" relates to arterial hypertension, capillary hypertension or vaso-hypertension.

Suitably, the term "pulmonary hypertension" relates to pulmonary arterial hypertension.

Furthermore it will be understood that pulmonary arterial hypertension relates to both primary arterial hypertension and to pulmonary arterial hypertension occurring secondary to pulmonary diseases such as chronic bronchitis, emphysema, kyphoscoliosis and conditions such as chronic mountain sickness.

When used herein the term "right heart failure" relates to disorders such as cor pulmonale and congenital abnormalities of the heart.

It will be appreciated that cor pulmonale often occurs secondary to certain lung diseases such as chronic bronchitis and emphysema.

Congenital abnormalities of the heart include disorders, such as atrial septal defect, tetralogy of fallot, venticular septal defect and persistent ductus arteriosus.

The administration of the Compound or a pharmaceutically acceptable salt thereof may be by way of oral, inhaled or parenteral administration, preferably by inhaled administration.

An amount effective to treat the disorders hereinbefore described depends on the usual factors such as the nature and severity of the disorders being treated and the weight of the mammal. However, a unit dose will normally contain 0.01 to 50 mg for example 0.01 to 10 mg, of the Compound, or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.1 to 10mg.

It is greatly preferred that the Compound or a pharmaceutically acceptable salt thereof is administered in the form of a unit-dose composition, such as a unit dose oral, parenteral or preferably inhaled composition.

Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

Preferably, compositions of the Compound are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, more preferably between 2 and 5 microns.

For parenteral administration, fluid unit dose forms are prepared containing the Compound and a sterile vehicle. The compound, depending on the vehicle and the concentration, can be either suspended or dissolved. Parenteral solutions are normally prepared by dissolving the Compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the Compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention. Where appropriate, small amounts of bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH, may be included.

As is common practice, the compositions will usually be accompanied by written or printed directions for use in the medical treatment concerned.

A particularly favoured form of the method of the invention is that wherein the Compound or a pharmaceutically acceptable salt thereof, or a pharmaceutically acceptable solvate thereof, is administered by inhalation. It will also be appreciated from the above that it is a further aspect of the present invention to provide the treatment of disorders associated with pulmonary hypertension and/or disorders associated with right heart failure, by inhalation of any such vasodilator.

Accordingly in a further aspect the invention provides the use of a vasodilator, in particular pinacidil, or where appropriate a pharmaceutically acceptable salt thereof, or a pharmaceutically acceptable solvate thereof, for the manufacture of a medicament for the treatment, by inhalation, of disorders associated with pulmonary hypertension and/or disorders associated with right heart failure.

The present invention further provides a pharmaceutical composition for use in the treatment and/or prophylaxis of disorders associated with pulmonary hypertension and/or disorders associated with right heart failure, which comprises a vasodilator, in particular pinacidil, or a pharmaceutically acceptable salt thereof, or a pharmaceutically acceptable solvate thereof, and, if required, a pharmaceutically acceptable carrier therefor.

Suitable compositions are unit dosage compositions as described above.

The term 'vasodilator' includes ganglion blockers, sympathetic nerve blockers, such as $\alpha_1$-adrenoceptor blockers, and direct vasodilators.

Suitable ganglion blockers include pentolinium, mecamylamine, trimetaphan and pempidine.

Suitable sympathetic nerve blockers include bethanidine, guanethidine, debrisoquine and such $\alpha_1$-adrenoceptor blockers as prazosin.

Suitable direct vasodilators include calcium channel blockers such as nifedipine.

Suitable direct vasodilators include potassium channel activators such as pinacidil. Other such compounds are N-(2-hydroxyethyl)nicotinamide nitrate ester and N-methyl-2-(3-pyridyl)-tetrahydrothiopyran-2-carbothioamide- 1-oxide.

Suitable direct vasodilators include diazoxide, minoxidil, and hydralazine.

The abovementioned vasodilators may be prepared using conventional methods eg as indicated in The Merck Index 10th Edition, N-(2-hydroxyethyl)nicotinamide nitrate ester may be prepared as disclosed in U.S. Pat. No. 4,200,640 and N-methyl-2-(3-pyridyl)-tetrahydrothiopyran-2-carbothioamide- 1-oxide may be prepared as disclosed in DD 210082 or Chemical Abstracts, 1984, 101:200235W.

A particularly favoured pharmaceutically acceptable composition is an inhalation composition, suitably in unit dosage form.

Such compositions may be prepared in the manner as hereinbefore described.

Pharmacological Data
Human Isolated Pulmonary Vasculature

Macroscopically normal human lung tissue was obtained from patients undergoing thoracic surgery for bronchial carcinoma. Following surgical removal, the pulmonary arteries were disected into rings and set up in an organ bath under isometric conditions using a 2g tension. Tissues were allowed to equilibrate for 1h and tone induced with 30mM potassium chloride. When the contraction had reached a maximum, the inhibitory effect of the test compound was examined in a cumulative protocol fashion ($10^{-8}$ to $2\times10^{-5}$M). The results were expressed as a percentage of the maximum relaxation induced by papavarine ($10^{-4}$M).

Results

Pinacidil induced concentration dependent relaxations from $10^{-6}$ to $2\times10^{-5}$M against tone induced by 30mM potassium. At $2\times10^{-5}$M, pinacidil had an intrinsic activity of 0.39 relative to the maximum relaxation produced by $10^{-4}$M papavarine.

We claim:

1. A method for the treatment of disorders associated with pulmonary hypertension or right heart failure in mammals, which method comprises administering to the mammal in need thereof a therapeutically effective amount of a vasodilator selected from the group consisting of ganglion blockers, sympathetic nerve blockers, and direct vasodilators, wherein said vasodilator is administered to said mammal by inhaling.

2. A method according to claim 1, wherein the vasodilator is selected from the group consisting of: pentolinium, mecamylamine, trimetaphan, pempidine, bethanidine, guanethidine, debrisoquine, prazosin, N-(2-hydroxyethyl) nicotinamide nitrate ester, N-methyl-2-(3-pyridyl)tetrahydrothiopyran- 2-carbothioamide-1-oxide, diazoxide, minoxidil and hydralazine.

3. A method according to claim 1, wherein the vasodilator is administered in unit dosage form.

4. A method according to claim 1, wherein the therapeutically effective amount is 0.0001 to 1 mg/kg/day.

5. The method according to claim 1, wherein the ganglion blocker is selected from the group consisting of pentolinium, mecamylamine, trimetaphan, and pempidine.

6. The method according to claim 1, wherein the sympathetic nerve blocker is selected from the group consisting of bethanidine, guanethidine, debrisoquine, and prazosin.

* * * * *